United States Patent [19]
Petrus et al.

[11] Patent Number: 5,417,224
[45] Date of Patent: May 23, 1995

[54] TAMPON AND METHOD FOR MANUFACTURING THE SAME

[75] Inventors: Edward J. Petrus; Maurice S. Conte, both of Austin, Tex.

[73] Assignee: Advanced Medical Instruments, Inc., Austin, Tex.

[21] Appl. No.: 63,906

[22] Filed: May 19, 1993

[51] Int. Cl.⁶ .................. A61F 6/06; A61F 13/15; A61F 13/20
[52] U.S. Cl. .................. 128/833; 128/839; 128/840; 128/918; 604/12; 604/358; 604/363; 604/904
[58] Field of Search .................. 604/1-2, 604/11-12, 904, 358, 363; 128/830, 832, 833, 834, 839, 840, 841, 918, DIG. 21

[56] References Cited
U.S. PATENT DOCUMENTS

| | | |
|---|---|---|
| 3,780,730 | 12/1973 | Weisman . |
| 3,949,752 | 4/1976 | Van Stee . |
| 4,186,742 | 2/1980 | Donald . |
| 4,309,997 | 1/1982 | Donald . |
| 4,360,013 | 11/1982 | Barrows .................. 128/832 |
| 4,393,871 | 7/1983 | Vorhamer . |
| 4,693,705 | 9/1987 | Gero . |
| 4,922,928 | 5/1990 | Burnhill . |
| 5,000,749 | 3/1991 | LeVeen et al. . |

*Primary Examiner*—Randall L. Green
*Assistant Examiner*—P. Zuttarelli
*Attorney, Agent, or Firm*—Conley, Rose & Tayon

[57] ABSTRACT

An improved tampon is provided having one or more loops placed entirely through the tampon for ease in insertion and removal of an attached spherical member into and from a body cavity. Moreover, the improved tampon can be impregnated at select depths with specific spermicides, anti-infectives, lubricants, hormones, antioxidants, amino acids, etc., to allow release of inner-impregnated fluids from the member into the body cavity. Closely controlled impregnation and/or coating of the tampon is achieved by a method of manufacture employing one or more sonic baths containing necessary impregnating and/or coating fluids.

12 Claims, 3 Drawing Sheets

TAMPON AND METHOD FOR MANUFACTURING THE SAME

BACKGROUND OF THE INVENTION

1. Field of the Invention

This invention relates to a tampon and more particularly to a tampon configured for easy insertion and removal, and having regions of spermicides, anti-infectives and lubricants placed within the tampon.

2. Background of the Relevant Art

It is well known that in recent years there has been a steady increase in the number of sexually transmitted diseases (STDs) and unwanted pregnancies in the U.S. and throughout the world. In an effort to stem the rise of unwanted pregnancies, many types of contraceptive devices are being utilized. Oral contraceptives and intrauterine devices (IUD) are two very popular contraceptive methods. However, not all women are capable of using oral contraceptives, and IUDs produce many documented side effects. Other types of contraceptives, or barrier contraceptives, have gained in popularity due to the rise of STDs. Popular barrier contraceptives include condoms, diaphragms, sponges, cervical caps, spermicidal creams, foams, foaming tablets, films and melting suppositories. A diaphragm and cervical cap must be fitted by trained medical personnel, whereas condoms require the participation of the partner. Foams, jellies, tablets and suppositories are often messy to use, and frequently cause irritation to the user and/or partner.

Developments in contraceptive methods allow a barrier, such as a sponge or tampon, to be impregnated with a spermicide. The impregnated barrier not only physically prevents the passage of sperm or STDs, but also chemically kills the sperm or infective agents associated with many STDs. A time-release spermicide can allow a single impregnated tampon to kill sperm throughout numerous sexual encounters and over a relatively long period of time.

As described in U.S. Pat. No. 4,393,871, gradual release of spermicide from a tampon can be achieved by placing the spermicide into the pre-polymer material during the polymerization of the tampon. The spermicide/surfactant is thereby molded to form the polyurethane tampon. In order to activate the tampon of Patent '871, tap water must be added at the site. Too large an amount of water can unduly dilute the spermicide, such as nonxylphenoxypoly (ethyleneoxy) ethanol, or "nonoxynol-9", possibly rendering it ineffective. Further, tap water at the site may be contaminated, or may contain chlorine which could possibly interfere with the nonoxynol-9 or cause infection. Conversely, too small an amount of water can cause a strong presence of nonoxynol-9, leading to irritation and allergic reaction as described in U.S. Pat. No. 4,693,705.

As taught in Patent '705, recent advances suggest a more controlled concentration of spermicide, such as nonoxynol-9. Accordingly, it is advantageous that the spermicide be placed already in solution within the sponge and at controlled concentration such that the spermicide is active and ready to use at the site. Mixing with tap water is therefore not required.

Impregnating a sponge with a solution such that it is ready to use at the site presents many advantages described above. However, the soaked tampon must maintain its shape as a physical barrier while packaged and during insertion. Further, it also must withstand shear forces during placement and subsequent removal. Current sponges which use a single string placed through only a portion of the sponge material can pull through the sponge upon removal. Examples of sponges which use only a small portion of their geometry for receiving a string or tied loop are described in U.S. Pat. Nos. 4,186,742; 4,309,997; and 4,693,705. Another exemplary attachment scheme showing a loop affixed to the outside surface of the sponge is taught in U.S. Pat. No. 4,393,871. A slight pull upon the string or loop can cause a single string shown in Patents '742 and '997 to pull through the body, can cause a loop shown in Patent '871 to pull from the body's outer surface, or a knot and surrounding small portion of the body shown in Patent '705 to dislodge from the body. A future source of infection may arise if any portion of the sponge material is allowed to remain in the body cavity for an extended period of time. "Toxic shock syndrome" may arise in instances where an infective site is allowed to remain within a body cavity, such as a vaginal canal, for an extended period of time.

A properly inserted and removed sponge or tampon not only enhances the benefits of the device, but also maintains long-term effect while positioned. Ease of positioning or insertion is equally important as maintaining the sponge's integrity during removal. A sponge, having a doughnut or flattened shape as shown in Patent '871 may easily fold thereby failing to present equal radial pressure against the cavity wall. A passage may therefore be formed in those areas voided of pressure as a result of the fold. An optimal shape appears to be spherical ball having radially expandable pressure against all sides of the cavity wall. However, the spherical ball will oftentimes be compressed to an outer dimension much less than the original expanded dimension during placement. As a result, spermicide impregnated within only the outer portion of the sponge may be flushed or squeezed from the sphere during placement. Absence of spermicide can thereby lead to an ineffective contraceptive device.

As defined herein, "spermicide" is a chemical placed in solution, and which provides a chemical barrier against sperm and sexually transmitted organisms responsible for STDs. Therefore, "spermicides" used herein include an anti-infective agent. Spermicide have, in many instances, been found to be active against herpes, gonorrhea, syphilis, trichomonas, candida, and even HIV. Popular spermicides include benzalkonium chloride, chlorhexidine, gluconate, menfegol, octoxynol and, as described above, nonoxynol-9. Nonoxynol-9 is a spermicide which acts by destroying the cell wall of the sperm, and is believed to act in the same manner on bacteria and viruses. Because it destroys the cell wall of sperm, bacteria and viruses, it can also cause some local irritation in both men and women using the product improperly, or in large dosages.

SUMMARY OF THE INVENTION

The problems outlined above are in large part solved by the improved tampon of the present invention. That is, the tampon hereof is spherical in shape and substantially resistant to severe folding or deformation during placement. Further, after placement, the tampon is radially conformable against the walls of a body cavity or vaginal canal of fluctuating inner diameter. Thus, the tampon is capable of retaining equal radial pressure against the body cavity wall. Moreover, the sponge is pre-packaged and shipped ready to use with a properly controlled solution of spermicide, anti-infectives, anti-fungals, anti-virals, hormones, amino acids and/or antioxidants impregnated as a solution therein. The tampon can be easily inserted and completely removed by utilizing a cord placed entirely through the sponge and encircling at least 40% cross-sectional area of the spherical tampon. The cord is shaped as a loop and presents ease of insertion by extending pressure between the sphere and the loop such that the sphere can be accurately and precisely placed in a compressed or deformed state. Once placed, the sphere expands and thereafter exits as a complete physical barrier within the cavity.

The tampon hereof is selectively impregnated using ultrasonic penetration of various solutions at controlled depths within the sphere. Spermicides and/or anti-infective agents can be ultrasonically impregnated deep into the sphere. The sonic frequency and magnitude can be carefully controlled to ensure proper depth of penetration into the sphere. A coating of slightly greater viscosity material can be placed on only the outer region or surface of the sphere after the tampon is deeply and fully impregnated with a controlled concentration of spermicide and/or anti-infectives, anti-fungals, anti-virals, hormones amino acids, and/or antioxidants. The outer coating includes a lubricant, wherein the lubricant can be impregnated into the sphere a controlled distance by varying the ultrasonic parameters used to place the lubricant. The lubricant is deposited on the lining of the cavity walls during insertion of the tampon, leaving the spermicide available as a chemical barrier against infective, foreign agents introduced into the cavity. The lubricant can contain hormones, amino acids, and/or antioxidant compounds which, when placed upon the cavity wall prevent tears or abrasions through use of the lubricant or, if a tear exists, can promote healing of the tear through use of a hormone, or medicinal agent.

Broadly speaking, the present invention contemplates an improved tampon comprising a porous spherical member having an outer region and an inner region, and a first passage placed completely through the member. A first cord is placed through the first passage and is fastened at both ends to form a loop. A spermicide is placed within the pores throughout the inner region of the member, and a lubricant of greater density than the spermicide is placed within the pores throughout the outer region of the member.

According to an alternative embodiment, the porous spherical member can include two passages, a first passage and a second passage. The first passage can accommodate a first cord placed through the passage to form a loop, while the second passage can accommodate a second cord placed through the passage to form a loop. Preferably, the second passage is placed completely through the member substantially perpendicular or orthogonal to the first passage and spaced a distance from the first passage. By placing the first and second passage perpendicular to each other, two loops can be formed through the passages which can allow the spherical member to be compressed between the inner surface of both loops to form a more evenly compressed, ready-to-insert member. Using two loops instead of one ensures that the spherical member does not fold as it is being heavily compressed for insertion into smaller cavity openings. However, it is understood that a spherical member having one loop can be placed without folding provided substantial compression is not needed and the user is careful during insertion.

The spherical member is selectively impregnated with various solutions such that the inner region of the member can be fully impregnated with a solution such as a spermicide at a concentration between 50 mg/cc to 1000 mg/cc. It is also important that the outer region, comprising between 10% to 20% cross-section of the member, be impregnated with a lubricant. The lubricant is preferably of greater density than the solution used to impregnate the inner region. Thus, the lubricant helps seal the openings of any imperfections or passageways existing throughout the member against movement of sperm or STDs therethrough. The lubricant effectively coats the outer surface and operates as a partial barrier between the body cavity opening and the inner pores of the member. Moreover, the coating provides lubrication to the body cavity, and is removed in the area which contacts the body cavity during insertion. Thus, spermicide-impregnated inner pores of the member allow release of spermicide to the surface areas removed of lubricant (i.e., at the interface between the spherical member and the body cavity wall).

The present invention further contemplates a method for manufacturing a tampon comprising the steps of cutting a spherical member from a block of polymeric foam material, and then placing at least one cord having two ends entirely through the member. Two ends of the cord can be fastened together to form a loop encircling a portion of the member. The member is then inserted into a bath containing between 50 mg/cc to 1000 mg/cc spermicide. An acoustic disturbance can then be sent through the bath to controllably impregnate the member. Thereafter, the member is removed from the bath and a coating of lubricant is placed across the outer surface of the member.

As defined herein, "tampon" refers to any porous member which can be inserted into a physiological cavity. The tampon includes any porous substance which is capable of being impregnated and/or coated. The tampon is capable of being placed into a body cavity of a human female or male between internal organs and an insertable physiological or non-physiological member. The tampon can be used to coat the cavity with hormones, amino acids, antioxidants, lubricants, etc. Further the tampon can receive solutions which will reduce or prevent unwanted pregnancies, transferral of disease, growth of virus, growth of fungus, etc. Certainly, tampon includes a sponge normally used for insertion into the vaginal canal of a human female.

BRIEF DESCRIPTION OF THE DRAWINGS

Other objects and advantages of the invention will become apparent upon reading the following detailed description and upon reference to accompanying drawings in which.

Figure 1:
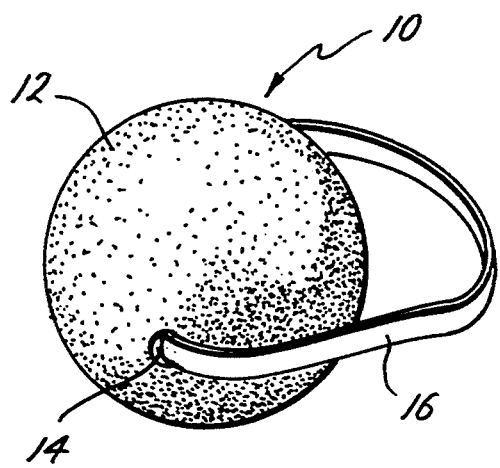
FIG. 1 is a perspective view of a tampon according to the present invention.

While the invention is susceptible to various modifications and alternative forms, specific embodiments thereof are shown by way of example in the drawings and will herein be described in detail. It should be understood, however, that the drawings and description thereto are not intended to limit the invention to the particular forms disclosed, but on the contrary, the intention is to cover all modifications, equivalents and alternatives falling within the spirit and scope of the present invention as defined by the appended claims.

DETAILED DESCRIPTION OF THE INVENTION

Turning now to the drawings, FIG. 1 illustrates a tampon 10 according to the present invention. Tampon 10 includes a spherical member 12 having a polymeric sponge-like structure. Member 12 can be of any size sufficient to be slightly compressed (i.e., radially compressed inward from its uncompressed size, so as to fit snugly within the body cavity after compression is released. Member 12 can be easily inserted into the cavity without the need for orientation. Further there is no need for a special applicator. The material of member 12 is preferably a soft, lightweight, physiologically inert polymeric foam of polyurethane, polyether, polyester, or the like, which is of a very fine porosity and which, when released from compression, will return to substantially its original shape. Such foam materials are known in the art. The tampon is preferably cut from a block of foam which results in a smooth, continuously porous outer and inner surface. As an example, spherical member 12 can be cut approximately 4.0 cm in diameter to be placed in a vaginal canal of a human female to cover the cervical area while permitting intercourse to occur. Four centimeters appears an optimal diameter for such an exemplary purpose.

Placed entirely through member 12 is a first passage 14 having a diameter of approximately 1.0 to 4.0 mm. A first cord 16 is configured to extend through passage 14 and can be joined together to form a loop. Cord 16 is composed of cotton, polyester, or any physiologically inert material which is soft yet sturdy enough to withstand stress after long periods of immersion within a solution. Cord 16 can be approximately 1.0 mm to 2.0 mm in diameter and several hundred mm. long depending upon the diameter of member 12. Cord 16 can either have a circular diameter or can be rectangular in cross-section as shown in FIG. 1. By forming a loop from cord 16, member 12 can be removed from the body cavity by grasping the loop and simply pulling the loop from the cavity. The loop and attached member 12 are substantially resistant to tearing due to the elongated surface area between which cord 16 and passage 14 abut adjacent one another. Furthermore, when grasped and pulled, cord 16 automatically compresses member 12 in an arcuate path formed along the longitudinal axis of passage 14. The compression, and arcuate path along passage 14 allows member 12 to be more easily inserted and removed along the compressed cross-section area.

Figure 2:
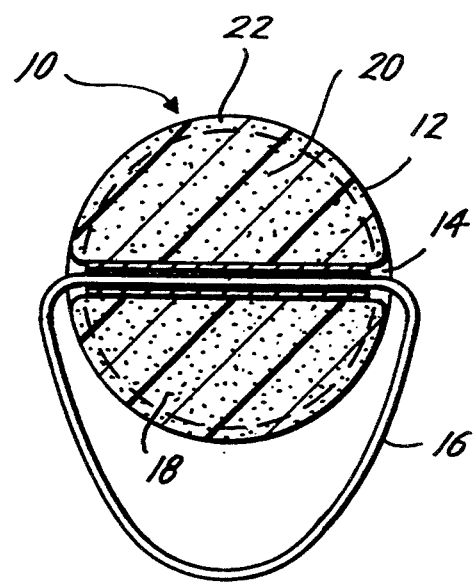
FIG. 2 is a cross-sectional view of a tampon according to the present invention.

Referring to FIG. 2, a cross-sectional view of member 12, passage 14 and cord 16 are shown. Cord 16, being flexible and resilient to tear, encircles a cross-sectional area 18 of at least 40% but less than 70% of the total cross-sectional area of member 12. By placing passage 14 through an area near the middle of sphere 12, sufficient cross-sectional area is encircled to ensure area 18 is not too small and not too large. If area 18 is small, it might become dislodged or tear during removal. Conversely, if area 18 is too large, then the area on the other side of passage 14, opposite area 18, might tear during removal. By placing passage 14 through an area near the center of member 12, there is a greater likelihood that member 12 will collapse along the thickest portion of the member causing more even compression throughout the sphere without folding the sphere.

FIG. 2 also illustrates an inner and an outer region 20 and 22, respectively. Inner region 20, as well as outer region 22, are sufficiently porous to receive a spermicide which will be safe and effective for physiological use, such as nonoxynol-9. It is understood, however, that other spermicides known in the art may also be used. Other potential spermicide candidates include sodium oxychlorosene, alkylphenoxy polyethoxy ethanol, benzalkonium chloride, etc. The inner and outer regions may also be impregnated with anti-infective agents including antibiotics such as bacitracin, neomycin, polymyxin B, penicillin, tetracycline, chloramphenicol, erythromycin, sulfonamid, nitrofurazone, and providone-iodine. Iodine may be dissolved in a surfactant such as nonoxynol-9 and impregnated into the tampon. Chlorhexidine gluconate may serve the same purpose. Other medications such as anti-inflammatory compounds including steroids, antifungal agents including micronazole, and anti-viral drugs including acyclovir or interferon may be incorporated in the tampon depending upon the desired therapeutic or prophylactic effect, and the time span for which the device provides therapy.

Placed on only the outer region 22 may be a combination of medications described above and lubricants/moisturizers. Furthermore, amino acids, hormones, and antioxidants may be placed within region 22. Lubrication for vaginal dryness includes glycerin, sorbic acid and mineral oil. Hormonal preparations for atrophic vaginitis may include estrogen and progesterone compounds. Amino acids may be added to treat cervicitis and cervical tears by facilitating would healing and epithelization. Antioxidants may include vitamin A or vitamin E. Preservatives and pH adjusters may also be added. An acid environment decreases sperm mobility and inactivates gonococcus. A deodorant, such as pectin, may also be added to the tampon for aromatic purposes. A perfume may also be added, as well as a flavoring agent in order to promote use of the tampon.

Outer region 22 is configured having similar porosity to inner region 22. The depth for which outer region exits and into which lubricants can be added is determined solely by the method for impregnating the desired lubricant material or compound. As will be described hereinbelow, the method preferably includes ultrasound for impregnating lubricant to a controlled distance within member 12 (i.e., only within outer region 22). The controlled impregnation depth is preferably between 10% to 20% of the cross-sectional diameter of member 12 directly adjacent the member's outer surface. Moreover, ultrasound provides a suitable advantage in impregnating a controlled concentration of spermicide/anti-infectives as well as a denser lubricant into the member. Further, ultrasound ensures the subsequent sonic placement of lubricant will drive further inward the spermicide/anti-infectives into the member. Sonic placement of lubricant within only the outer region ensures any tears, holes, or imperfections in the sponge-like porous material will be fully sealed near the member surface.

Figure 3:
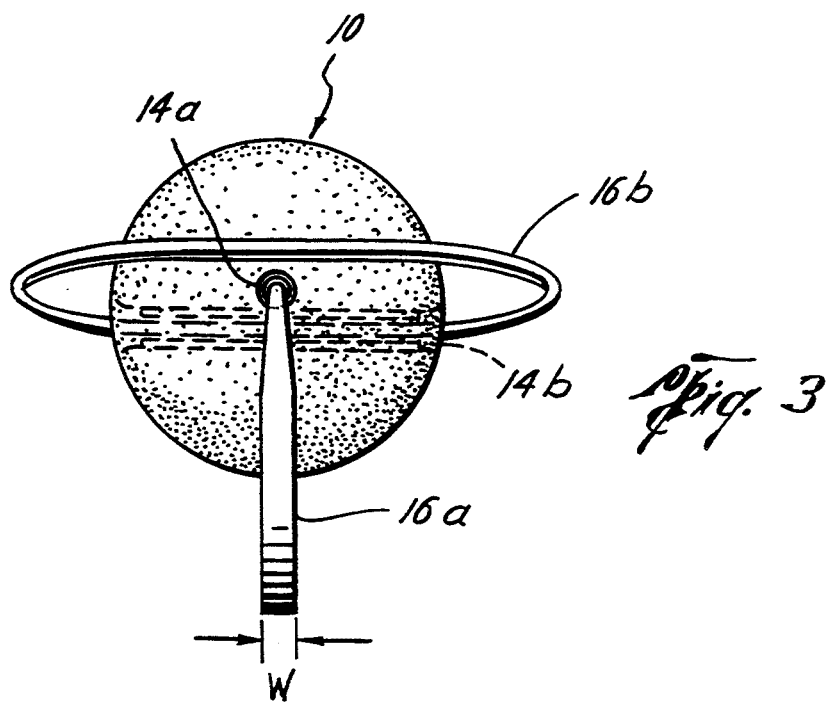
FIG. 3 is a perspective view of an alternative embodiment of a tampon according to the present invention.

Turning now to FIG. 3, an alternative embodiment of tampon 10 is shown. Specifically, tampon 10 can be made having one or more passages 14. In the embodiment of FIG. 3, two passages are shown. First passage 14a is adapted for receiving first cord 16a, whereas second passage 14b is adapted for receiving second cord 16b. First and second cords 16a and 16b can be configured as straps. A suitable geometry for each strap is 1.0 mm thickness, 4.0 mm width, and 150 mm length. The straps are compressible along width W within each respective passage. A compressible strap can provide greater shear strength during times in which either the first, second or both cords are pulled. It is important that the cord which is pulled does not break or pull away from the tampon. Utilizing straps, which are compressible or which deform into a circular passage 14a or 14b, provide additional surface area adjacent the respective passage in order to resist large shear forces which often cause breakage.

Figure 4:
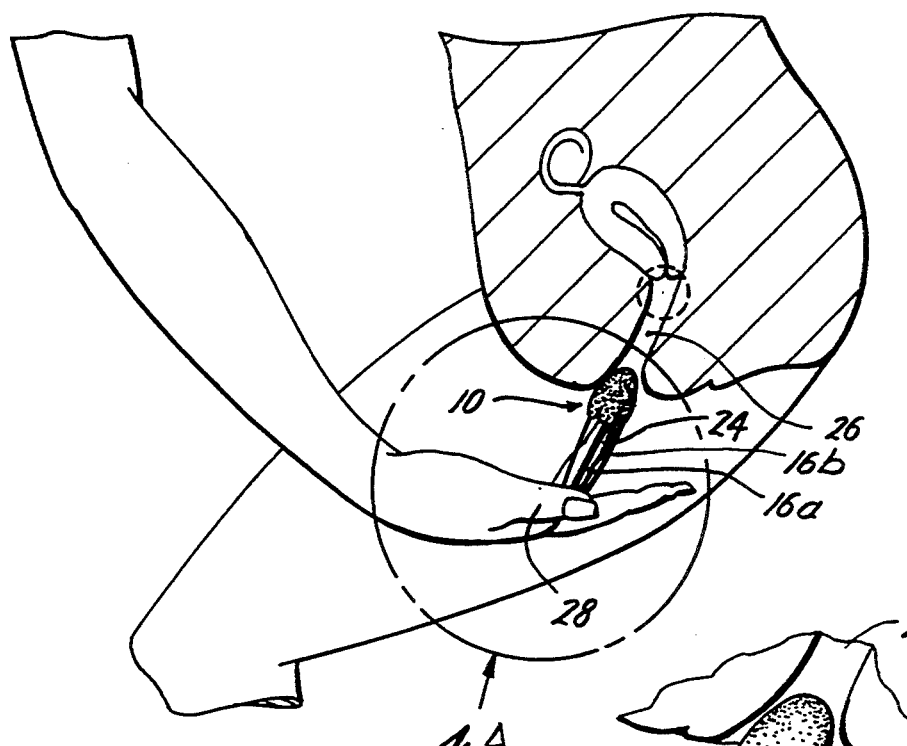
FIG. 4 is a tampon shown in a compressed state for insertion into a body cavity according to the present invention.

Turning now to FIG. 4, tampon 10 is shown appropriately grasped for placement into a body cavity 26 such as a vaginal canal. Tampon 10 is shown having first and second cords 16a and 16b grasped between the forefinger 24 and thumb 28 of the user such that the distal end of forefinger 24 compresses against the outer surface of member 12. A sufficient amount of compression will distort member 12 along the longitudinal axis of the first and second passages 14a and 14b. Accordingly, sufficient force between member 12 and first-/second cords 16a and 16b allows member 12 to compress radially inward and along an axis aligned with the body cavity and the direction of insertion. Member 12 will distort from its spherical shape to a cross-sectional diameter less than the uncompressed sphere in the direction of insertion. The compressed geometry can therefore be placed into a body cavity of lesser diameter than the uncompressed sphere thereby allowing the compressed geometry to radially expand equally against the entire surrounding cavity wall. It is understood that in lieu of two cords 16a and 16b, insertion can be carried out with only one cord in certain circumstances. For example, if the body cavity opening 26 is fairly large and not significantly smaller than uncompressed member 12 cross-sectional diameter, then an undue amount of compression need not occur. In this instance, necessary compression of member 12 can take place with only minimal pressure between member 12 and a single cord 16. Minimal pressure will not cause deleterious folds to occur within the member.

Figure 5:
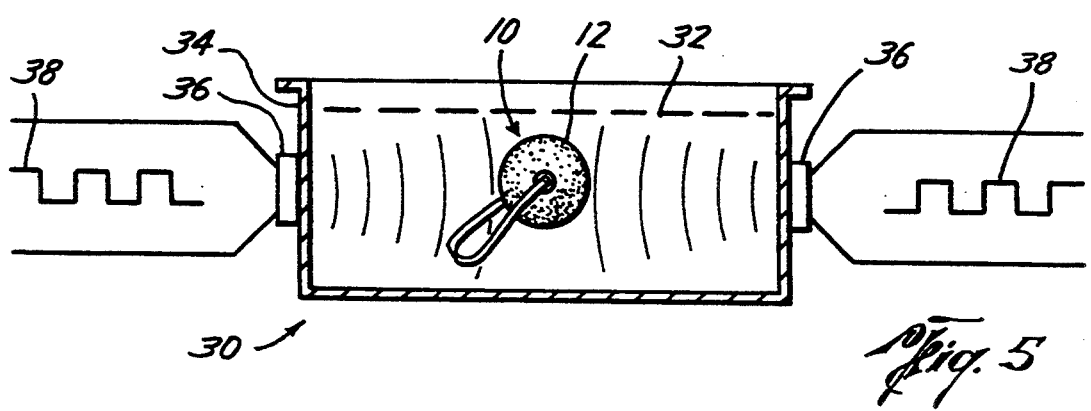
FIG. 5 is a tampon placed within a ultrasonic bath for receiving sonic waves according to the present invention.

Referring now to FIG. 5, an important advantage of tampon 10 manufacture is the ability to selectively impregnate member 12 with various fluids and at various depths. Impregnation is preferably achieved using a sonic bath 30 filled with an appropriate solution 32. A carefully controlled concentration of solution 32 can be placed within container 34 of bath 30. Container 34 has an opening through which tampon 10 can be placed into solution 32. Any solution which can be impregnated as a spermicide, anti-infective, anti-viral, anti-fungal, etc., can be housed within container 34 and falls within the spirit and scope of the present invention.

Sonic transducers 36 are placed on one or more walls of container 34. Each transducer 36 is in acoustic contact with solution 32. Transducers 36 receive an electric signal 38 and, in response to that signal, produces an acoustic disturbance within solution 32 and at a controlled depth within porous member 12. The amount of acoustic disturbance within member 12 can be varied in magnitude and frequency depending upon changes in electric signal 38. Disturbances at frequencies greater than 20 KHz and at large peak-to-peak voltages produce sufficient vibration upon the porous structure to allow substantial penetration across the entire cross-sectional area of member 12. Changes in magnitude and frequency of signal 38 correspond to changes in the depth of penetration of solution 32 within member 12. For example, lower frequency, lower magnitude signals 38 may cause the solution to impregnate at a different depth than if signals 38 are higher in frequency and magnitude.

Figure 6:
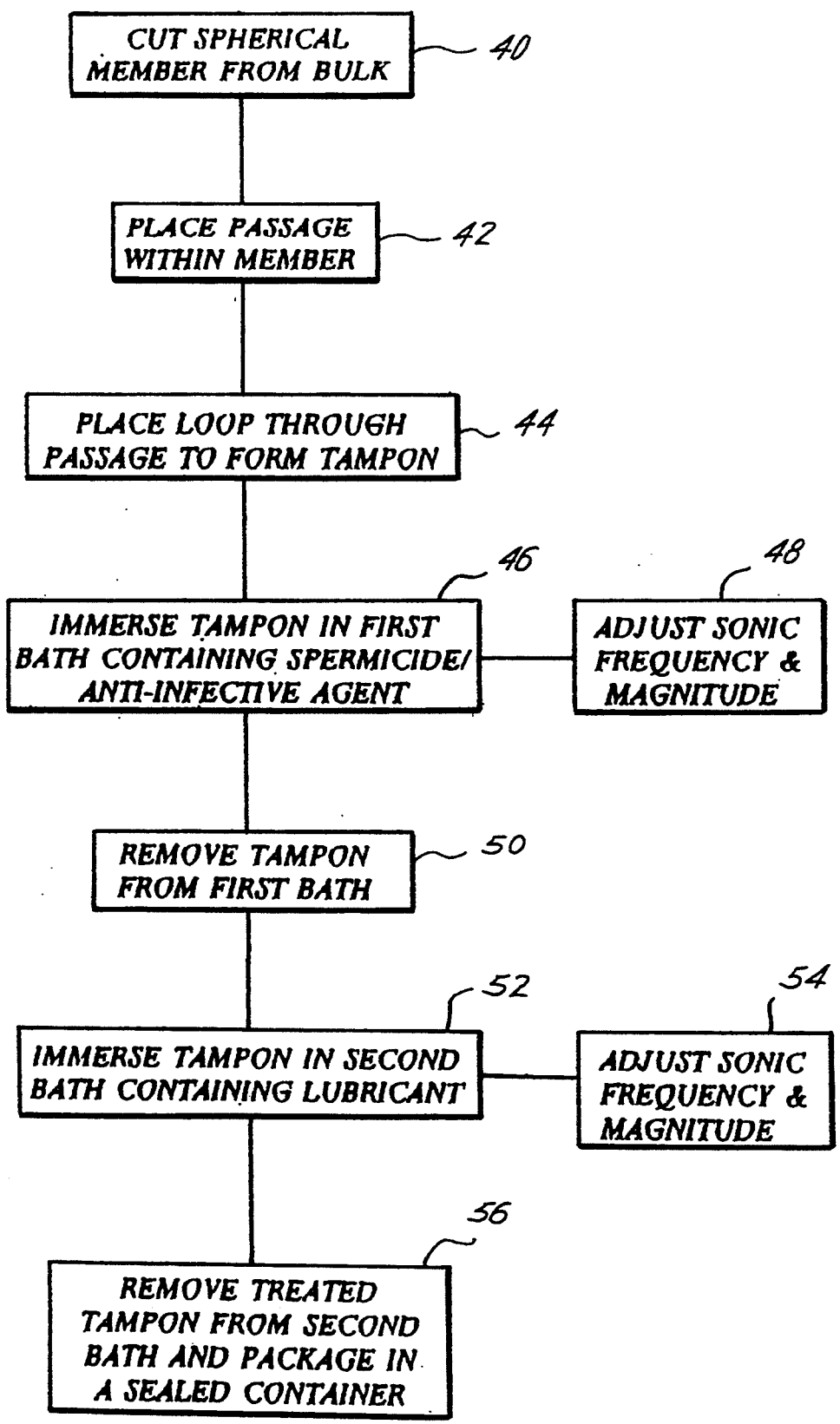
FIG. 6 is a flow diagram of various steps utilized in manufacturing a tampon according to the present invention.

Referring now to FIG. 6, a flow diagram of various steps used in manufacturing a properly coated and impregnated tampon 10 is shown. It is preferred that member 12 be cut from a bulk polymeric foam material 40. By cutting the spherical member 12 instead of forming the member within a mold, member 12 exhibits an open pore structure at the outer surface which will allow more solution to impregnate into the member than if the outer surface is molded. It is well know that a molding process can cause formation of a skin and force the outer surface pores to close, leaving them relatively impervious to impregnation and, conversely, impervious to dispersal of spermicide from the pores. After the spherical member is obtained, a passage is placed within the member shown by step 42. It is understood that one or more passages can be placed within the member depending upon the body cavity environment into which member 12 is placed. If a large amount of inward radial compression is desired, then two or more passage may be necessary. Regardless of the number of passages formed, each passage can accommodate a loop placed through respective passages to form a tampon, as shown in step 44. Each passage is preferably offset from each other and perpendicular to one another. By offsetting the passages, no more than one passage is placed within a specific cross-sectional area of member 12. Thus, there is less likelihood that the passages will tear the member at the cross-sectional area containing the passages.

Figure 4A:
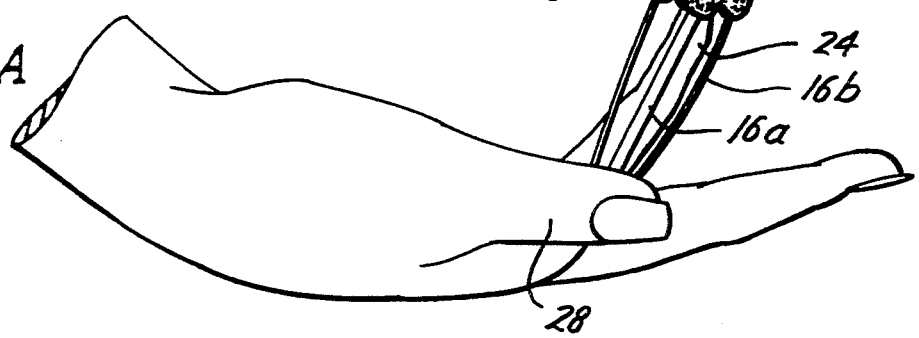
FIG. 4A is a detail view along area A of FIG. 4.

After tampon 10 is formed, it is then immersed in a first bath containing a solution of spermicide/anti-infectives. The first bath is subjected to a specific sonic frequency and magnitude necessary to impregnate both the inner and outer regions to select depths. Sonic frequency can easily be changed by changing electric signals placed upon the transducers of the first bath, as shown by block 48. Once tampon 10 is impregnated within the first bath to a specific depth, it is then removed from the first bath and placed within a second bath containing a coating material or lubricant, as shown by steps 50 and 52. Lubricant is placed at a controlled depth within the outer region by adjusting the sonic frequency and magnitude, shown by step 54. An important advantage of the present invention is the ability to accommodate various fluids of dissimilar density and to place those fluids at select depths by merely changing the sonic frequency and magnitude of the corresponding electric signal. Controlled impregnation of various fluids having dissimilar viscosity and density is a suitable advantage of the improved tampon 10 and method of manufacture according to the present invention. After tampon 10 is selectively impregnated within various solutions and at various depths, it is then removed from the bath, as shown in step 56, and then placed in a hermetically sealed container. Tampon 10 is then ready for use by simply removing the tampon from the container and inserting the tampon into a corresponding body cavity as shown in FIGS. 4 and 4A.

Tampon 10 is easily inserted into the cavity area using an extended forefinger 24 placed between member 12 and the inner surface of one or more cords 16. Tampon is inserted before sexual intercourse and should remain within the cavity for at least two to six hours after intercourse. During insertion, moisturizer/lubricant agents within the outer region also coat the cavity wall. Throughout the recommended wearing period, spermicide/anti-infectives are released from member 12 and into the cavity area. Tampon 10 is removed by grasping the flexible cord with the fingers and pulling the attached member 12 from cavity 28. Cords 16a and 16b may be adhesively bonded to one or more areas within their respective first and second passages 14a and 14b. However, it is not necessary that they be bonded, and in some instances, cords 16a and 16b should remain freely moving through their respective passages. Certainly, tampons employing non-bonded cords would be easier to manufacture than if the cords are bonded.

It will be appreciated to those skilled in the art having the benefit of this disclosure that this invention is believed to be capable of insertion into numerous body cavities of various sizes and shapes. Furthermore, it is also to be understood that the form of the invention shown and described is to be taken as presently preferred embodiments. Various modifications and changes may be made without departing from the spirit and scope of the invention as set forth in the claims. An exemplary modification might be one which uses only one passage and cord, or more than two passages and two cords. Moreover, the coating of a more dense lubricant on only the outer region of the tampon can be accomplished by spray coating or any other form of coating. Ultrasonic impregnation, however, provides closer control in the depth of coating as well as allowing specific fluids to fully impregnate the porous member. If close tolerance of coating depth is not necessary, then spray coating would be adequate. It is intended that the following claims be interpreted to embrace all such modifications and changes.

What is claimed is:

1. A tampon comprising:
   a porous spherical member having an outer region and an inner region, and a first passage placed completely through said member, said inner region is configured radially inside said outer region;
   a first cord extending through said first passage and fastened at both ends to form a loop encircling at least 40% of a total cross-sectional area of the spherical member;
   a spermicide placed within the pores throughout the inner region of said member; and
   a lubricant placed within the pores throughout the outer region of said member.

2. The tampon as recited in claim 1, wherein said first passage comprises a wall surface upon which said first cord is fastened.

3. The tampon as recited in claim 1, wherein said member comprises an outer surface and a cross-sectional diameter, said outer region includes 10% to 20% of said diameter directly adjacent said outer surface.

4. The tampon as recited in claim 1, wherein said member comprises an outer surface and a cross-sectional diameter, said inner region includes 80% to 90% of said diameter spaced from said outer surface by said outer region.

5. The tampon as recited in claim 1, further comprising:
   a second passage placed completely through said member substantially orthogonal to and spaced a distance from said first passage; and
   a second cord extending through said second passage and fastened at both ends to form a loop.

6. The tampon as recited in claim 3, wherein said second passage comprises a wall surface upon which said second cord is fastened.

7. A tampon configured for insertion by a user into a body cavity comprising:
   a porous spherical member having an outer region completely surrounding an inner region, said outer region is impregnated with a lubricant and said inner region is impregnated with a spermicide, and a first passage placed completely through said member; and
   a loop placed through said first passage and encircling a first portion of said spherical member, said member is capable of collapsing along an axis perpendicular to said first passage when said loop is drawn from said member during use.

8. The tampon as recited in claim 7, wherein said first passage comprises a wall surface upon which said first cord is fastened.

9. The tampon as recited in claim 7, wherein said member comprises an outer surface and a cross-sectional diameter, said outer region includes 10% to 20% of said diameter directly adjacent said outer surface.

10. The tampon as recited in claim 7, wherein said member comprises an outer surface and a cross-sectional diameter, said inner region includes 80% to 90% of said diameter spaced from said outer surface by said outer region.

11. The tampon as recited in claim 7, further comprising:
    a second passage placed completely through said member substantially orthogonal to and spaced a distance from said first passage; and
    a second loop placed through said second passage and encircling a second portion of said spherical member, said member is capable of collapsing along an axis perpendicular to said first and second passages to form a reshaped member of collapsed diameter perpendicular a body cavity.

12. The tampon as recited in claim 11, wherein said second passage comprises a wall surface upon which said second cord is fastened.

* * * * *